United States Patent
Pasquet et al.

(10) Patent No.: US 10,925,826 B2
(45) Date of Patent: Feb. 23, 2021

(54) COSMETIC COMPOSITION COMPRISING A VINYLFORMAMIDE/VINYLFORMAMINE COPOLYMER, A CELLULOSE-BASED THICKENING POLYMER AND AN AMPHOTERIC OR ZWITTERIONIC SURFACTANT

(71) Applicant: L'OREAL, Paris (FR)

(72) Inventors: Dorothee Pasquet, Bois Colombes (FR); Cecile Bebot, Asnieres (FR)

(73) Assignee: L'OREAL, Paris (FR)

( * ) Notice: Subject to any disclaimer, the term of this patent is extended or adjusted under 35 U.S.C. 154(b) by 28 days.

(21) Appl. No.: 14/767,928

(22) PCT Filed: Feb. 12, 2014

(86) PCT No.: PCT/EP2014/052742
§ 371 (c)(1),
(2) Date: Aug. 14, 2015

(87) PCT Pub. No.: WO2014/124977
PCT Pub. Date: Aug. 21, 2014

(65) Prior Publication Data
US 2016/0000686 A1    Jan. 7, 2016

Related U.S. Application Data

(60) Provisional application No. 61/773,197, filed on Mar. 6, 2013.

(30) Foreign Application Priority Data

Feb. 15, 2013 (FR) .................................. 13 51324

(51) Int. Cl.
| | |
|---|---|
| *A61K 8/81* | (2006.01) |
| *A61K 8/44* | (2006.01) |
| *A61Q 5/06* | (2006.01) |
| *A61K 8/73* | (2006.01) |
| *A61K 8/04* | (2006.01) |
| *A61K 8/39* | (2006.01) |
| *B65D 83/14* | (2006.01) |

(52) U.S. Cl.
CPC .............. *A61K 8/817* (2013.01); *A61K 8/046* (2013.01); *A61K 8/39* (2013.01); *A61K 8/44* (2013.01); *A61K 8/442* (2013.01); *A61K 8/731* (2013.01); *A61Q 5/06* (2013.01); *B65D 83/14* (2013.01); *A61K 2800/22* (2013.01); *A61K 2800/48* (2013.01); *A61K 2800/592* (2013.01); *A61K 2800/594* (2013.01); *A61K 2800/87* (2013.01)

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,528,378 A | 10/1950 | Mannheimer |
| 2,723,248 A | 11/1955 | Wright |
| 2,781,354 A | 2/1957 | Mannheimer |
| 3,579,629 A | 5/1971 | Pasero et al. |
| 3,589,978 A | 6/1971 | Kamal et al. |
| 3,716,633 A | 2/1973 | Viout et al. |
| 3,734,874 A | 5/1973 | Kibler et al. |
| 3,779,993 A | 12/1973 | Kibler et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |

(Continued)

FOREIGN PATENT DOCUMENTS

| | | |
|---|---|---|
| DE | 2330956 A1 | 1/1974 |
| DE | 19540853 A1 | 5/1997 |

(Continued)

OTHER PUBLICATIONS

Pascale et al. (FR 2926989 A1) English translation.*
International Search Report for PCT/EP2014/052740, dated May 12, 2014.
International Search Report for PCT/EP2014/052742, dated May 9, 2014.
English language abstract for FR 2357241 (Feb. 3, 1978).
English language abstract for FR 2926984 (Aug. 7, 2009).
English language abstract for FR 2926989 (Aug. 7, 2009).
French Search Report for counterpart Application No. FR 07154210, dated Nov. 13, 2007.

(Continued)

*Primary Examiner* — Aradhana Sasan
*Assistant Examiner* — Quanglong N Truong
(74) *Attorney, Agent, or Firm* — The Marbury Law Group, PLLC

(57) ABSTRACT

The present invention relates to a cosmetic composition comprising: one or more vinylformamide/vinylformamine copolymers comprising: from 10 to 95 mol % of units of formula A1, and from 90 to 5 mol % of units of formula A2, one or more cellulose-based thickening polymers; and one or more amphoteric or zwitterionic surfactants. It also relates to the use of this composition for shaping and/or fixing the hairstyle, to a cosmetic treatment process for the hair using said composition and also to a particular cosmetic set.

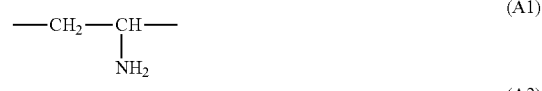

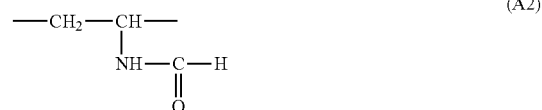

18 Claims, No Drawings

(56) References Cited

U.S. PATENT DOCUMENTS

| | | | |
|---|---|---|---|
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,119,680 A | 10/1978 | Vachon | |
| 4,128,631 A | 12/1978 | Lundmark et al. | |
| 4,129,711 A | 12/1978 | Viout et al. | |
| 4,131,576 A | 12/1978 | Iovine et al. | |
| 4,137,180 A | 1/1979 | Naik et al. | |
| 4,137,208 A | 1/1979 | Elliott | |
| 4,165,367 A | 8/1979 | Chakrabarti | |
| 4,223,009 A | 9/1980 | Chakrabarti | |
| 4,282,203 A | 8/1981 | Jacquet et al. | |
| 4,289,752 A | 9/1981 | Mahieu et al. | |
| 4,300,580 A | 11/1981 | O'Neill et al. | |
| 4,342,744 A | 8/1982 | Arai et al. | |
| 4,693,935 A | 9/1987 | Mazurek | |
| 4,713,236 A | 12/1987 | Hoover et al. | |
| 4,728,571 A | 3/1988 | Clemens et al. | |
| 4,764,363 A | 8/1988 | Bolich, Jr. | |
| 4,874,554 A | 10/1989 | Lange et al. | |
| 4,972,037 A | 11/1990 | Garbe et al. | |
| 4,973,656 A | 11/1990 | Blount | |
| 5,538,717 A | 7/1996 | La Poterie | |
| 5,575,991 A | 11/1996 | Kischka et al. | |
| 5,632,977 A | 5/1997 | Chandran et al. | |
| 5,660,816 A | 8/1997 | Adams et al. | |
| 5,662,893 A | 9/1997 | George et al. | |
| 5,674,479 A | 10/1997 | George et al. | |
| 5,753,759 A | 5/1998 | Hartmann et al. | |
| 6,106,813 A | 8/2000 | Mondet et al. | |
| 6,166,093 A | 12/2000 | Mougin et al. | |
| 6,231,876 B1 * | 5/2001 | Niessner | A61Q 5/12 424/401 |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 6,630,133 B1 | 10/2003 | Dupuis | |
| 7,063,834 B2 | 6/2006 | Mougin et al. | |
| 7,919,106 B2 | 4/2011 | Giroud et al. | |
| 8,956,631 B2 | 2/2015 | Giroud et al. | |
| 2001/0055580 A1 | 12/2001 | Belli et al. | |
| 2002/0150546 A1 | 10/2002 | Mougin et al. | |
| 2003/0191271 A1 | 10/2003 | Mondet et al. | |
| 2003/0199642 A1 | 10/2003 | Schneider et al. | |
| 2004/0197279 A1 * | 10/2004 | Bleckmann | A61K 8/39 424/59 |
| 2004/0228809 A1 * | 11/2004 | Birkel | A61Q 5/065 424/47 |
| 2005/0129646 A1 | 6/2005 | Vic et al. | |
| 2005/0245684 A1 | 11/2005 | Daniel et al. | |
| 2005/0276777 A1 | 12/2005 | Lalleman et al. | |
| 2006/0286057 A1 | 12/2006 | Cannell et al. | |
| 2007/0081964 A1 | 4/2007 | Muller et al. | |
| 2007/0107141 A1 | 5/2007 | Nguyen et al. | |
| 2007/0110690 A1 | 5/2007 | Nguyen et al. | |
| 2008/0182773 A1 | 7/2008 | Gauweiler et al. | |
| 2008/0200359 A1 | 8/2008 | Smets et al. | |
| 2008/0260666 A1 | 10/2008 | Giroud et al. | |
| 2009/0202465 A1 | 8/2009 | Mougin et al. | |
| 2009/0269295 A1 | 10/2009 | Benabdillah et al. | |
| 2009/0274641 A1 * | 11/2009 | Mathonneau | A61K 8/731 424/70.13 |
| 2011/0097278 A1 | 4/2011 | Verboom | |
| 2011/0186070 A1 | 8/2011 | Verboom | |
| 2011/0224309 A1 * | 9/2011 | Hunter | A61K 8/042 514/772.1 |

FOREIGN PATENT DOCUMENTS

| | | |
|---|---|---|
| DE | 102005014293 A1 | 9/2006 |
| EP | 0412704 A2 | 2/1991 |
| EP | 0412707 A1 | 2/1991 |
| EP | 0582152 A2 | 2/1994 |
| EP | 0619111 A1 | 10/1994 |
| EP | 0637600 A1 | 2/1995 |
| EP | 0648485 A1 | 4/1995 |
| EP | 0688557 A2 | 12/1995 |
| EP | 0751162 A1 | 1/1997 |
| EP | 1779894 A1 | 5/2007 |
| EP | 1977732 A1 | 10/2008 |
| EP | 2149365 A2 | 2/2010 |
| FR | 1222944 A | 6/1960 |
| FR | 1400366 A | 5/1965 |
| FR | 1564110 A | 4/1969 |
| FR | 1580545 A | 9/1969 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A1 | 2/1978 |
| FR | 2393573 A1 | 1/1979 |
| FR | 2439798 A1 | 5/1980 |
| FR | 2743297 A1 | 7/1997 |
| FR | 2926984 A1 | 8/2009 |
| FR | 2926986 A1 | 8/2009 |
| FR | 2926988 A1 | 8/2009 |
| FR | 2926989 A1 | 8/2009 |
| GB | 839805 A | 6/1960 |
| GB | 922457 A | 4/1963 |
| GB | 1021400 A | 3/1966 |
| GB | 1408388 A | 10/1975 |
| GB | 1572626 A | 7/1980 |
| JP | 2002-255756 A | 9/2002 |
| LU | 75370 A1 | 2/1978 |
| LU | 75371 A1 | 2/1978 |
| WO | 93/23009 A1 | 11/1993 |
| WO | 93/23446 A2 | 11/1993 |
| WO | 94/03510 A1 | 2/1994 |
| WO | 95/00578 A1 | 1/1995 |
| WO | 95/18191 A1 | 7/1995 |
| WO | 96/03969 A1 | 2/1996 |
| WO | 97/08261 A1 | 3/1997 |
| WO | 97/20899 A1 | 6/1997 |
| WO | 02/15854 A1 | 2/2002 |
| WO | 2007/003784 A1 | 1/2007 |
| WO | 2010/028153 A2 | 3/2010 |
| WO | 2014/124976 A1 | 11/2014 |

OTHER PUBLICATIONS

JP 2002-255756A, Machine Translation, retrieved online on Jun. 21, 2011, pp. 1-9.
Gebelein, Charles C., "Cosmetic and Pharmaceutical Applications of Polymers," Springer Science+Business Media New York, 1991, p. 31.
Non-Final Office Action for copending U.S. Appl. No. 12/362,848, dated Oct. 5, 2011.
Final Office Action for copending U.S. Appl. No. 12/362,848, dated Jun. 6, 2012.
Non-Final Office Action for copending U.S. Appl. No. 12/362,848, dated Sep. 30, 2013.
Final Office Action for copending U.S. Appl. No. 12/362,848, dated Jun. 27, 2014.
Non-Final Office Action for U.S. Appl. No. 12/362,848, dated Jun. 18, 2015.
Non-Final Office Action for copending U.S. Appl. No. 12/362,848, dated Nov. 17, 2016.
Non-Final Office Action for copending U.S. Appl. No. 12/362,848, dated Apr. 24, 2017.
Non-Final Office Action for copending U.S. Appl. No. 12/362,848, dated Oct. 16, 2017.
Non-Final Office Action for copending U.S. Appl. No. 14/767,925, dated Feb. 17, 2017.
Final Office Action for copending U.S. Appl. No. 14/767,925, dated Aug. 22, 2017.
French Search Report for counterpart Application No. FR 08/50607, dated Sep. 24, 2008.
Final Office Action for copending U.S. Appl. No. 12/362,848 (now abandoned), dated Apr. 23, 2018.

(56) References Cited

OTHER PUBLICATIONS

Final Office Action for copending U.S. Appl. No. 14/767,925, dated Jun. 21, 2018.
Non-Final Office Action for copending U.S. Appl. No. 14/767,925, dated Dec. 21, 2018.
Final Office Action for copending U.S. Appl. No. 14/767,925, dated Feb. 18, 2020.

* cited by examiner

COSMETIC COMPOSITION COMPRISING A VINYLFORMAMIDE/VINYLFORMAMINE COPOLYMER, A CELLULOSE-BASED THICKENING POLYMER AND AN AMPHOTERIC OR ZWITTERIONIC SURFACTANT

CROSS REFERENCE TO RELATED APPLICATIONS

This is a national stage application of PCT/EP2014/052742, filed internationally on Feb. 12, 2014, which claims priority to U.S. Provisional Application No. 61/773,197, filed on Mar. 6, 2013; as well as French Application No. 1351324, filed on Feb. 15, 2013, all of which are incorporated herein by reference in their entireties.

The present invention relates to a cosmetic composition comprising one or more vinylformamide/vinylformamine copolymers, one or more cellulose-based thickening polymers and one or more amphoteric or zwitterionic surfactants.

The present invention also relates to a cosmetic treatment process for the hair, in particular a process for fixing and/or shaping the hair using the abovementioned composition.

Finally, the present invention relates to the use of this composition for cosmetic hair treatment, and in particular for hair styling, i.e. shaping and/or fixing the hairstyle.

Styling products are normally used to construct and structure the hairstyle and to give it shape retention. They are usually in the form of lotions, gels, foams, creams, sprays, etc. The corresponding compositions generally comprise one or more film-forming polymers or "fixing polymers". These polymers allow the formation of a coating film on the hair, thus providing form retention of the hairstyle.

However, the fixing-polymer films thus formed have the drawback of being relatively friable, thereby limiting the shape retention of the hairstyle over time, and causing the formation on the hair of unaesthetic residues.

Thus, conventional styling products result in fixing of the hairstyle and styling effects which gradually fade over time. In particular, when the product is applied in the morning, the styling effects gradually fade during the course of the day. The following day, the styling effects are weak, or even non-existent.

To remedy this problem, it is known practice to incorporate, into styling products, polymers with a very high fixing capacity, and/or to increase the concentration of fixing polymer. However, the use of such extremely fixing products causes a certain number of drawbacks. In particular, these products result in the hair having a dry and rough feel, and are difficult to remove with shampoo.

Patent application EP 2 149 365 describes compositions comprising vinylformamide/vinylformamine copolymers and thickening polymers, for in particular producing styling gels.

Moreover, when foams are used, they have more or less firm textures with a limited hold in the hand.

There is therefore a need for hair compositions which make it possible to obtain long-lasting fixing of the hairstyle, with styling effects that last throughout the day or even for several days, while at the same time being easy to remove with shampoo and providing a pleasant cosmetic feel, and in particular a smooth feel.

There is also a need to obtain foams with an improved texture.

The applicant has now discovered that, surprisingly, the combination of a vinylformamide/vinylformamine copolymer with a non-ionic fixing polymer and a cationic surfactant in a cosmetic composition makes it possible to obtain a cosmetic hair composition which provides improved styling properties. In particular, such a combination makes it possible to obtain styling products which provide long-lasting fixing of the hairstyle, while at the same time being easy to remove and providing the hair with a pleasant cosmetic feel. It also makes it possible to obtain a composition in the form of a foam with an expanded texture that is easy to hold.

A subject of the present invention is thus a cosmetic composition comprising:
one or more vinylformamide/vinylformamine copolymers comprising:
from 10 to 95 mol % of units of the following formula A1:

and from 90 to 5 mol % of units of the following formula A2:

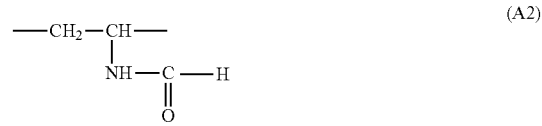

one or more cellulose-based thickening polymers; and
one or more amphoteric or zwitterionic surfactants.

Advantageously, this composition is non-washing, i.e. it contains less than 5% by weight in total of anionic surfactants and of non-ionic surfactants.

The compositions according to the invention make it possible to obtain styling compositions which provide long-lasting fixing and make it possible in particular to obtain expanded foams which have good styling and cosmetic properties.

Other subjects, characteristics, aspects and advantages of the invention will become even more clearly apparent on reading the description and examples that follow.

According to the invention, the cosmetic composition comprises one or more vinylformamide/vinylformamine copolymers, one or more cellulose-based thickening polymers and one or more amphoteric or zwitterionic surfactants.

Vinylformamide/Vinylformamine Copolymers

The vinylformamide/vinylformamine copolymer(s) which can be used in the compositions according to the invention preferably comprise(s) from 10 to 60 mol % of units of formula A1 and more particularly from 20 to 40 mol %.

The vinylformamide/vinylformamine copolymer(s) according to the invention preferably comprise(s) from 30 to 90 mol % of units of formula A2 and more particularly from 60 to 80 mol %.

The copolymers according to the invention can be obtained, for example, by partial hydrolysis of polyvinylformamide. This hydrolysis may be performed in an acidic or basic medium.

The vinylformamide/vinylformamine copolymer(s) according to the invention can optionally comprise one or more additional monomer units. In this case, the latter preferably represent(s) less than 20 mol % of the copolymer.

According to one preferred embodiment, the vinylformamide/vinylformamine copolymer(s) according to the invention consist(s) solely of units of formula A1 and of units of formula A2.

The weight-average molecular weight of said copolymer, measured by light diffraction, can vary from 10 000 to 30 000 000 g/mol, preferably from 40 000 to 1 000 000 g/mol and more particularly from 100 000 to 500 000 g/mol.

The cationic charge density of said copolymer can vary from 2 meq/g to 20 meq/g, preferably from 2.5 to 15 meq/g and more particularly from 3.5 to 10 meq/g.

By way of example of vinylformamide/vinylformamine copolymers which can be used in the compositions according to the invention, mention may be made, inter alia, of the products sold under the name Luviquat 9030 by the company BASF, and the products provided under the names Lupamin 9010, Lupamin 5095 and Lupamin 1595 by the company BASF.

The vinylformamide/vinylformamine copolymer(s) is (are) present in the compositions according to the invention in proportions preferably ranging from 0.01% to 20% by weight, more preferentially from 0.1% to 10% by weight and more particularly from 0.1% to 5% by weight, relative to the total weight of the composition.

Cellulose-Based Thickening Polymer

As indicated previously, the cosmetic composition according to the invention comprises one or more cellulose-based thickening polymers.

For the purpose of the present invention, the term "thickening polymer" is intended to mean a polymer which, when introduced at 1% in a pure aqueous solution or an aqueous-alcoholic solution containing 30% ethanol, and at pH=7, makes it possible to achieve a viscosity of at least 100 cps and preferably of at least 500 cps, at 25° C. and at a shear rate of 1 s$^{-1}$. This viscosity may be measured using a cone/plate viscometer (Haake R600 rheometer or the like).

Preferably, these polymers increase, through their presence, the viscosity of the compositions into which they are introduced by at least 50 cps and preferably 200 cps, at 25° C. and at a shear rate of 1 s$^{-1}$.

The term "cellulose-based" polymer is intended to mean, according to the invention, any polysaccharide compound having in its structure sequences of glucose residues bonded together via β-1,4 linkages.

The cellulose-based thickening polymers can be chosen from unsubstituted celluloses, in particular in microcrystalline form, and cellulose derivatives which may be anionic, cationic, amphoteric or non-ionic.

Among these cellulose-based polymers, cellulose ethers, cellulose esters and cellulose ester ethers are distinguished.

Among the cellulose esters are inorganic esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/inorganic esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the non-ionic cellulose ethers without a $C_{10}$-$C_{30}$ fatty chain, i.e. which are "non-associative", mention may be made of ($C_1$-$C_4$)alkylcelluloses, such as methylcelluloses and ethylcelluloses (for example, Ethocel standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy($C_1$-$C_4$)alkyl-($C_1$-$C_4$)alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hydroxybutylmethylcelluloses.

Among the anionic cellulose ethers without a fatty chain, mention may be made of (poly)carboxy($C_1$-$C_4$)alkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers without a fatty chain, mention may be made of cationic cellulose derivatives such as cellulose copolymers or cellulose derivatives grafted with a water-soluble quaternary ammonium monomer, and described in particular in patent U.S. Pat. No. 4,131,576, such as (poly)hydroxy($C_1$-$C_4$)alkyl celluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

Among the cellulose-based thickening polymers which can be used in the composition according to the invention, cellulose ethers, and preferably non-ionic cellulose ethers, are more particularly preferred.

Hydroxyalkylcelluloses, and in particular hydroxyethylcelluloses, will especially be used.

The cellulose-based thickening polymer(s) is (are) preferably present in an amount ranging preferably from 0.01% to 10% by weight, even better still from 0.02% to 5% by weight and even more preferentially from 0.04% to 1% by weight, relative to the total weight of the composition.

Amphoteric or Zwitterionic Surfactants

As previously indicated, the composition according to the invention comprises one or more amphoteric or zwitterionic surfactants as defined hereinafter.

The amphoteric or zwitterionic surfactants capable of being used in the present invention can in particular be derivatives of optionally quaternized secondary or tertiary aliphatic amines comprising at least one anionic group, such as, for example, a carboxylate, sulfonate, sulfate, phosphate or phosphonate group, and in which the aliphatic group or at least one of the aliphatic groups is a linear or branched chain comprising from 8 to 22 carbon atoms.

Mention may in particular be made of ($C_8$-$C_{20}$)alkylbetaines, sulfobetaines, ($C_8$-$C_{20}$)alkylamido($C_1$-$C_6$)alkylbetaines such as cocoamidopropylbetaine, and ($C_8$-$C_{20}$)alkylamido($C_1$-$C_6$)alkylsulfobetaines.

Among the optionally quaternized secondary or tertiary aliphatic amine derivatives that may be used, mention may also be made of the products having the following respective structures (IA) and (IB):

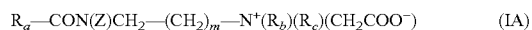

$$R_a\text{—CON}(Z)CH_2\text{—}(CH_2)_m\text{—}N^+(R_b)(R_c)(CH_2COO^-) \quad (IA)$$

in which:

$R_a$ represents a $C_{10}$-$C_{30}$ alkyl or alkenyl group derived from an acid $R_a$COOH preferably present in hydrolysed coconut oil, or a heptyl, nonyl or undecyl group, $R_b$ represents a β-hydroxyethyl group, and $R_c$ represents a carboxymethyl group;

m is equal to 0, 1 or 2; and

Z represents a hydrogen atom or a hydroxyethyl or carboxymethyl group.

$$R_a\text{—CON}(Z)CH_2\text{—}(CH_2)_m\text{—}N(B)(B') \quad (IB)$$

in which:

B represents —CH$_2$CH$_2$OX',

X' represents the —CH$_2$—COOH, CH$_2$—COOZ', —CH$_2$CH$_2$—COOH, or —CH$_2$CH$_2$—COOZ' group, or a hydrogen atom, B' represents —(CH$_2$)$_z$—Y', with z=1 or 2, Y' represents —COOH, —COOZ', or the —CH$_2$—CHOH—SO$_3$H or —CH$_2$—CHOH—SO$_3$Z' group, Z' represents an ion resulting from an alkali metal or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, R$_{a'}$ represents a C$_{10}$-C$_{30}$ alkyl or alkenyl group of an acid R$_a$COOH preferably present in hydrolysed linseed oil or coconut oil, or an alkyl group, in particular a C$_{17}$ group, and its iso form, or an unsaturated C$_{17}$ group, m' is equal to 0, 1 or 2, Z represents a hydrogen atom or a hydroxyethyl or carboxymethyl group.

These compounds are also classified in the CTFA dictionary, 5th edition, 1993, under the names sodium cocoamphodiacetate, disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, cocoamphodipropionic acid, and hydroxyethylcarboxymethylcocamidopropylamine.

By way of example, mention may be made of the cocoamphodiacetate sold by the company Rhodia under the trade name Miranol® C2M concentrate or under the trade name Miranol Ultra C 32 and the product sold by the company Chimex under the trade name Chimexane HA.

Use may also be made of compounds of formula (IC):

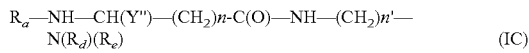

R$_a$—NH—CH(Y'')—(CH$_2$)$n$-C(O)—NH—(CH$_2$)$n'$—N(R$_d$)(R$_e$)    (IC)

in which:

R$_{a''}$ represents a C$_{10}$-C$_{30}$ alkyl or alkenyl group of an acid R$_{a''}$—C(O)OH, which is preferably present in hydrolysed linseed oil or coconut oil;

Y'' represents the group —C(O)OH, —C(O)OZ'', —CH$_2$—CH(OH)—SO$_3$H or the group —CH$_2$—CH(OH)—SO$_3$—Z'', with Z'' representing a cationic counterion resulting from an alkali metal or alkaline-earth metal, such as sodium, an ammonium ion or an ion resulting from an organic amine;

R$_d$ and R$_e$ represent, independently of each other, a C$_1$-C$_4$ alkyl or hydroxyalkyl radical; and n and n' denote, independently of each other, an integer ranging from 1 to 3.

Mention may in particular be made of the compound classified in the CTFA dictionary under the name sodium diethylaminopropyl cocoaspartamide and sold by the company Chimex under the name Chimexane HB.

Preferably, the amphoteric or zwitterionic surfactants are chosen from betaines and the compounds of formula (IB) and mixtures thereof.

Preferentially, the amphoteric or zwitterionic surfactants are chosen from cocoamidopropylbetaines, cocoamphodiacetates and hydroxyethylcarboxymethylcocamidopropylamine, alone or as a mixture.

The composition according to the invention preferably comprises the amphoteric or zwitterionic surfactant(s) in an amount ranging from 0.01% to 20% by weight, in particular from 0.1% to 10% by weight and better still from 0.15% to 5% by weight, relative to the total weight of the composition.

The composition according to the invention preferably comprises an amphoteric or zwitterionic surfactant(s)/cellulose-based thickening polymer(s) weight ratio ranging from 0.01 to 10 and even better still from 0.01 to 5.

The compositions of the invention can contain one or more additional fixing polymers other than the vinylformamide/vinylformamine copolymers and than the cellulose-based polymers of the invention.

For the purpose of the invention, the term "fixing polymer" is intended to mean any polymer that is capable, by application to the hair, of giving a shape to the head of hair or of holding the hair in an already acquired shape.

The additional fixing polymer(s) used in the context of the invention may be anionic, amphoteric, cationic or non-ionic.

The anionic fixing polymers generally used are polymers comprising groups derived from carboxylic acid, sulfonic acid or phosphoric acid and have a number-average molecular weight of between approximately 500 and 5 000 000.

The carboxylic groups are provided by unsaturated monocarboxylic or dicarboxylic acid monomers such as those corresponding to the formula:

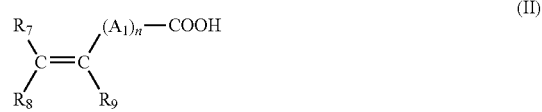

(II)

in which n is an integer from 0 to 10, A$_1$ denotes a methylene group, optionally connected to the carbon atom of the unsaturated group or to the neighbouring methylene group when n is greater than 1, via a heteroatom such as oxygen or sulfur, R$_7$ denotes a hydrogen atom, or a phenyl or benzyl group, R$_8$ denotes a hydrogen atom or a lower alkyl or carboxyl group, and R$_9$ denotes a hydrogen atom, a lower alkyl group or a —CH$_2$—COOH, phenyl or benzyl group.

In the abovementioned formula, a lower alkyl group preferably denotes a group having 1 to 4 carbon atoms and in particular methyl and ethyl groups.

The anionic fixing polymers comprising carboxylic groups which are preferred according to the invention are:

A) Copolymers of acrylic or methacrylic acid or salts thereof.

Among these polymers, mention may be made of copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described in particular in French patent No.1 222 944 and German patent application No. 2 330 956, the copolymers of this type comprising an optionally N-alkylated and/or hydroxyalkylated acrylamide unit in their chain as described in particular in Luxembourg patent application Nos. 75370 and 75371. Mention may also be made of copolymers of acrylic acid and of C$_1$-C$_4$ alkyl methacrylate and terpolymers of vinylpyrrolidone, of acrylic acid and of C$_1$-C$_{20}$ alkyl methacrylate, for example lauryl methacrylate, such as the product sold by the company ISP under the name Acrylidone® LM (INCI name VP/acrylates/lauryl methacrylate copolymer), acrylic acid/ethyl acrylate/

N-t-butylacrylamide terpolymers, such as the products Ultrahold® Strong and Ultrahold® 8 sold by the company BASF (INCI name Acrylates/t-butylacrylamide copolymer), methacrylic acid/ethyl acrylate/tert-butyl acrylate terpolymers, such as the products sold under the names Luvimer® 100 P or Luvimer® PRO 55 by the company BASF (INCI name Acrylates copolymer), copolymers of methacrylic acid and of ethyl acrylate, such as the products sold under the names Luvimer® MAE or Luviflex® Soft by the company BASF (INCI name Acrylates copolymer), acrylic acid/butyl acrylate/methyl methacrylate terpolymers, such as the product sold under the name Balance® CR by the company Akzo Nobel (INCI name Acrylates copolymer), and the copolymers of methacrylic acid and of methyl methacrylate sold under the name Eudragit® L 100 by the company Rohm Pharma (INCI name Acrylates copolymer). Mention may also be made of branched block polymers containing (meth) acrylic acid monomers, such as the product sold under the name Fixate® G-100L by the company Lubrizol (INCI name AMP-acrylates/allyl methacrylate copolymer);

B) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid. Such polymers are described, inter alia, in French patent Nos. 1 222 944, 1 580 545, 2 265 782, 2 265 781, 1 564 110 and 2 439 798. Commercial products which fall into this category are the products Resyn® 28-2930 and 28-1310 sold by the company Akzo Nobel (INCI names VA/crotonates/vinyl decanoate copolymer and VA/crotonates copolymer, respectively). Mention may also be made of the products Luviset® CA 66 sold by the company BASF, Aristoflex® A60 sold by the company Clariant (INCI name VA/crotonates copolymer) and Mexomere® PW or PAM sold by the company Chimex (INCI name VA/vinyl butyl benzoate/crotonates copolymer);

C) copolymers of monounsaturated $C_4$-$C_8$ carboxylic acids or anhydrides selected from:
copolymers comprising (i) one or more maleic, fumaric or itaconic acids or anhydrides and (ii) at least one monomer chosen from vinyl esters, vinyl ethers, vinyl halides, phenylvinyl derivatives, or acrylic acid and its esters, the anhydride functional groups of these copolymers optionally being monoesterified or monoamidated. Such polymers are described, in particular, in U.S. Pat. Nos. 2,047, 398, 2,723,248 and 2,102,113, and GB patent No. 839 805. Commercial products are in particular those sold under the names Gantrez® AN or ES by the company ISP, such as Gantrez® ES 225 (INCI name Ethyl ester of PVM/MA copolymer) or Gantrez® ES 425L (INCI name Butyl ester of PVM/MA copolymer);
copolymers comprising (i) one or more maleic, citraconic or itaconic anhydride units and (ii) one or more monomers chosen from allyl or methallyl esters, optionally comprising one or more acrylamide, methacrylamide, α-olefin, acrylic or methacrylic ester, acrylic or methacrylic acid or vinylpyrrolidone groups in their chain, the anhydride functional groups of these copolymers optionally being monoesterified or monoamidated.
These polymers are described, for example, in French patent Nos. 2 350 384 and 2 357 241 by the Applicant;
D) polyacrylamides comprising carboxylate groups.

The fixing polymers comprising units derived from sulfonic acid can be chosen from:

A') homopolymers and copolymers comprising vinylsulfonic, styrenesulfonic, naphthalenesulfonic or acrylamidoalkylsulfonic units.
These polymers can in particular be chosen from:
salts of polyvinylsulfonic acid having a molecular weight of between approximately 1000 and 100 000, as well as copolymers with an unsaturated comonomer, such as acrylic or methacrylic acids and their esters, as well as acrylamide or its derivatives, vinyl ethers and vinylpyrrolidone;
polystyrenesulfonic acid salts such as the sodium salts that are sold for example under the name Flexan® II by Akzo Nobel (INCI name Sodium polystyrene sulfonate).
These compounds are described in patent FR 2 198 719;
polyacrylamidosulfonic acid salts, such as those mentioned in patent U.S. Pat. No. 4,128,631, and more particularly the polyacrylamidoethylpropanesulfonic acid sold under the name Rheocare® HSP-1180 by Cognis (INCI name polyacrylamidomethylpropane sulfonic acid);

B') sulfonic polyesters, these polymers being advantageously obtained by polycondensation of at least one dicarboxylic acid, of at least one diol or of a mixture of diol and of diamine, and of at least one difunctional monomer comprising a sulfonic function. Among these polymers, mention may be made of:
linear sulfonic polyesters such as those described in patent application Nos. U.S. Pat. Nos. 3,734,874, 3,779,993, 4,119,680, 4,300,580, 4,973,656, 5,660,816, 5,662,893 and U.S. Pat. No. 5,674,479. Such polymers are, for example, the products Eastman® AQ38S Polymer, Eastman® AQ55S Polymer and Eastman® AQ48 Ultra Polymer sold by the company Eastman Chemical (name Polyester-5) which are copolymers obtained from diethylene glycol, from 1,4-cyclohexanedimethanol, from isophthalic acid and from sulfoisophthalic acid salt;
branched sulfonic polyesters such as those described in patent applications WO 95/18191, WO 97/08261 and WO 97/20899. Such compounds are, for example, the products Eastman® AQ10D Polymer (name Polyester-13) or Eastman® AQ1350 Polymer provided by the company Eastman Chemical (name Polyester-13).

According to the invention, the anionic fixing polymers are preferably chosen from copolymers of acrylic acid, such as the acrylic acid/ethyl acrylate/N-tert-butylacrylamide terpolymers sold in particular under the name Ultrahold® Strong by the company BASF, copolymers derived from crotonic acid, such as vinyl acetate/vinyl tert-butylbenzoate/crotonic acid terpolymers and the crotonic acid/vinyl acetate/vinyl neododecanoate terpolymers sold in particular under the name Resyn 28-2930 by the company Akzo Nobel, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the names Gantrez® ES 425L or ES 225 by the company ISP, the copolymers of methacrylic acid and of ethyl acrylate sold under the name Luvimer® MAE by the company BASF, and the vinyl acetate/crotonic acid copolymers sold under the name Luviset® CA 66 by the company BASF, and the vinyl acetate/crotonic acid copolymers grafted with polyethylene glycol sold under the name Aristoflex® A60 by the company Clariant, the vinylpyrrolidone/acrylic acid/lauryl methacrylate terpolymers sold under the name Acrylidone® LM by the company ISP, the polymer sold under the name Fixate® G-100L by the company Lubrizol, the vinyl acetate/crotonic acid/vinyl p-tert-butylbenzoate copolymers sold under the names Mexomere® PW or PAM by the company Chimex.

The cationic fixing polymers that can be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Among these polymers, mention may be made more particularly of the following cationic polymers:

(1) homopolymers or copolymers derived from acrylic or methacrylic esters or amides and comprising at least one of the units of the following formulae:

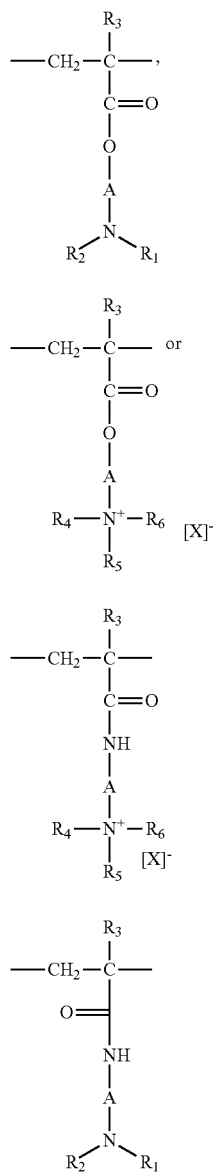

in which:

$R_3$ denotes a hydrogen atom or a $CH_3$ radical;

A is a linear or branched alkyl group comprising from 1 to 6 carbon atoms or a hydroxyalkyl group comprising from 1 to 4 carbon atoms;

$R_4$, $R_5$ and $R_6$, which may be identical or different, represent an alkyl group containing from 1 to 18 carbon atoms or a benzyl radical;

$R_1$ and $R_2$, which are identical or different, each represent a hydrogen atom or an alkyl group having from 1 to 6 carbon atoms;

X denotes a methosulfate anion or a halide such as chloride or bromide.

The copolymers of family (1) also contain one or more units derived from comonomers that may be chosen from the family of acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyl-lactams such as vinylpyrrolidone or vinylcaprolactam, and vinyl esters.

Thus, among these copolymers of family (1), mention may be made of:

quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755 or Gafquat® 755N (INCI name Polyquaternium-11), or alternatively the products known as Copolymer® 845, 958 and 937 sold by ISP (INCI name VP/dimethylaminoethyl methacrylate copolymer). These polymers are described in detail in French patents 2 077 143 and 2 393 573, fatty-chain polymers containing a vinylpyrrolidone unit, such as the products sold under the name Styleze® W2OL and Styleze® W10 by the company ISP (INCI name Polyquaternium-55), dimethylaminoethyl methacrylate/vinylcaprolactam/vinylpyrrolidone terpolymers, such as the products sold under the names Advantage HC 37 or Gaffix® VC 713 by the company ISP (INCI name Vinyl caprolactam/VP/dimethylaminoethyl methacrylate copolymer), and quaternized vinylpyrrolidone/dimethylaminopropylmethacrylamide copolymers, such as the products sold under the name Gafquat® HS 100 by the company ISP (name Polyquaternium-28);

(2) cationic guar gum derivatives, preferably comprising quaternary ammonium, such as those described in American patents 3 589 578 and 4 031 307, for instance guar gums containing trialkylammonium catatonic groups. Such products are sold in particular under the trade names Jaguar® C13 S, Jaguar® C 15 and Jaguar® C 17 by the company Rhodia (INCI name Guar hydroxypropyltrimonium chloride);

(3) quaternary copolymers of vinylpyrrolidone and of vinylimidazole; mention may be made, for example, of vinylpyrrolidone/methyl vinylimidazolium chloride copolymers, such as the products sold by the company BASF under the names Luviquat® FC550 or FC370, Luviquat® Excellence, Luviquat® Style (INCI name Polyquaternium-16), or vinylpyrrolidone/vinylimidazolium methosulfate/vinylcaprolactam terpolymers, such as the product Luviqut® Hold sold by the company BASF (INCI name Polyquaternium-46).

(4) chitosans or salts thereof; the salts that can be used are, in particular, chitosan acetate, lactate, glutamate, gluconate or pyrrolidonecarboxylate.

Among these compounds, mention may be made of the chitosan pyrrolidonecarboxylate sold under the name Kytamer® PC by the company Amerchol (INCI name Chitosan PCA).

The amphoteric fixing polymers that can be used in accordance with the invention can be chosen from polymers comprising units B and C distributed randomly in the polymer chain, where B denotes a unit derived from a monomer comprising at least one basic nitrogen atom and C denotes a unit derived from an acid monomer comprising one or more carboxylic or sulfonic groups, or alternatively B and C can denote groups derived from carboxybetaine or sulfobetaine zwitterionic monomers; B and C can also denote a cationic polymer chain comprising primary, secondary, tertiary or quaternary amine groups, in which at least one of the amine groups carries a carboxylic or sulfonic group connected via a hydrocarbon group, or alternatively B and C form part of a chain of a polymer comprising an α,β-dicarboxylic ethylene unit in which one of the carboxylic groups has been made to react with a polyamine comprising one or more primary or secondary amine groups.

The amphoteric fixing polymers corresponding to the definition given above that are more particularly preferred are chosen from the following polymers:

(1) copolymers containing acidic vinyl units and basic vinyl units, such as those resulting from the copolymerization of a monomer derived from a vinyl compound bearing a carboxylic group such as, more particularly, acrylic acid, methacrylic acid, maleic acid, α-chloroacrylic acid, and of a basic monomer derived from a substituted vinyl compound containing at least one basic atom, such as, more particularly, dialkylaminoalkyl methacrylate and acrylate, dialkylaminoalkylmethacrylamide and acrylamide. Such compounds are described in American patent No. 3 836 537.

(2) polymers comprising units derived from:
a) at least one monomer chosen from acrylamides or methacrylamides substituted on the nitrogen atom with an alkyl group,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic, methacrylic, crotonic, itaconic, maleic and fumaric acid and alkyl monoesters, having 1 to 4 carbon atoms, of maleic or fumaric acid or anhydride.

The preferred basic comonomers are aminoethyl, butylaminoethyl, N,N'-dimethylaminoethyl and N-tert-butylaminoethyl methacrylates.

The copolymers of which the INCI name is Octylacrylamide/acrylates/butylaminoethyl methacrylate copolymer, such as the products sold under the names Amphomer®, Amphomer® LV71 or Balance® 47 by the company Akzo Nobel, are particularly used;

(3) crosslinked and acylated polyaminoamides partially or totally derived from polyaminoamides of general formula:

(III)

in which $R_{10}$ represents a divalent group derived from a saturated dicarboxylic acid, a mono- or dicarboxylic aliphatic acid containing an ethylenic double bond, an ester of a lower alkanol having 1 to 6 carbon atoms of these acids, or a group derived from the addition of any one of said acids to a bis(primary) or bis(secondary) amine, and Z denotes a group derived from a bis(primary), mono(secondary) or bis(secondary) polyalkylene-polyamine and preferably represents:

a) in proportions of from 60 to 100 mol %, the group:

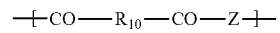
(IV)

where x=2 and p=2 or 3, or alternatively x=3 and p=2, this group being derived from diethylenetriamine, from triethylenetetramine or from dipropylenetriamine;

b) in proportions of from 0 to 40 mol %, the group (IV) above in which x=2 and p=1 and which is derived from ethylenediamine, or the group derived from piperazine:

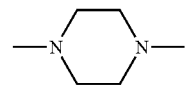

c) in proportions of from 0 to 20 mol %, the —NH—$(CH_2)_6$—NH— group deriving from hexamethylenediamine, these polyaminoamides being crosslinked by addition reaction of a difunctional crosslinking agent chosen from epihalohydrins, diepoxides, dianhydrides and bis-unsaturated derivatives, using from 0.025 to 0.35 mol of crosslinking agent per amine group of the polyaminoamide and acylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, and acids containing an ethylenic double bond such as, for example, acrylic acid, methacrylic acid and itaconic acid. The alkane sultones used in the acylation are preferably propane sultone or butane sultone; the salts of the acylating agents are preferably the sodium or potassium salts;

(4) polymers comprising zwitterionic units of formula:

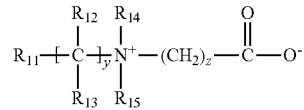
(V)

in which $R_{11}$ denotes a polymerizable unsaturated group such as an acrylate, methacrylate, acrylamide or methacrylamide group, y and z represent an integer from 1 to 3, $R_{12}$ and $R_{13}$ represent a hydrogen atom, or a methyl, ethyl or propyl group, and $R_{14}$ and $R_{15}$ represent a hydrogen atom or an alkyl group such that the sum of the carbon atoms in $R_{14}$ and $R_{15}$ does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

Mention may be made, by way of example, of methyl methacrylate/methyl dimethylcarboxymethylammonioethyl methacrylate copolymers, such as the product sold under the name Diaformer Z-301N or Z-301W by the company Clariant (INCI name Acrylates copolymer);

(5) polymers derived from chitosan comprising monomer units corresponding to the following formulae:

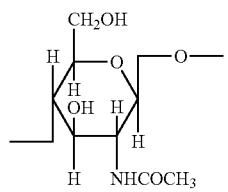
(D)

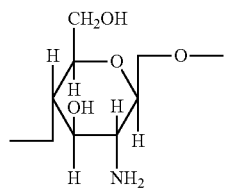
(E)

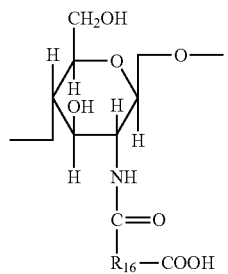
(F)

the unit (D) being present in proportions of between 0 and 30%, the unit (E) in proportions of between 5% and 50% and the unit (F) in proportions of between 30% and 90%, it being understood that, in this unit (F), $R_{16}$ represents a group of formula:

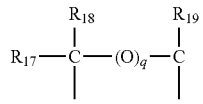

in which, if q=0, $R_{17}$, $R_{18}$ and $R_{19}$, which may be identical or different, each represent a hydrogen atom, a methyl, hydroxyl, acetoxy or amino residue, a monoalkylamine residue or a dialkylamine residue that are optionally interrupted with one or more nitrogen atoms and/or optionally substituted with one or more amine, hydroxyl, carboxyl, alkylthio or sulfonic groups, or an alkylthio residue in which the alkyl group bears an amino residue, at least one of the groups $R_{17}$, $R_{18}$ and $R_{19}$ being, in this case, a hydrogen atom;

or, if q=1, $R_{17}$, $R_{18}$ and $R_{19}$ each represent a hydrogen atom, and also the salts formed by these compounds with bases or acids;

(6) polymers containing units corresponding to general formula (VI) are described, for example, in French patent 1 400 366:

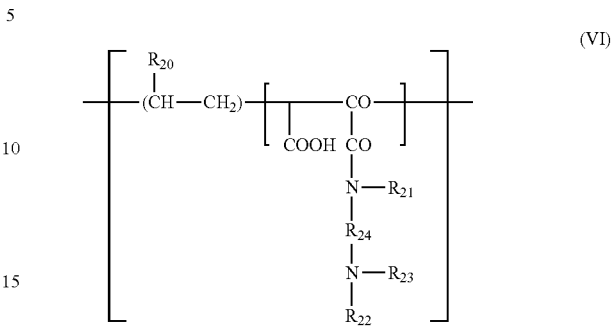
(VI)

in which $R_{20}$ represents a hydrogen atom, a $CH_3O$, $CH_3CH_2O$ or phenyl group, $R_{21}$ denotes a hydrogen atom or a lower alkyl group such as methyl or ethyl, $R_{22}$ denotes a hydrogen atom or a $C_1$-$C_6$ lower alkyl group such as methyl or ethyl, $R_{23}$ denotes a $C_1$-$C_6$ lower alkyl group such as methyl or ethyl or a group corresponding to the formula: —$R_{24}$—$N(R_{22})_2$, $R_{24}$ representing a group —$CH_2$—$CH_2$—, —$CH_2$—$CH_2$—$CH_2$— or —$CH_2$—$CH(CH_3)$—, $R_{22}$ having the meanings mentioned above;

(7) polymers derived from the N-carboxyalkylation of chitosan, such as N-carboxymethyl chitosan or N-carboxybutyl chitosan, for instance the product sold under the name Chitoglycan by the company Sinerga SPA (INCI name Carboxymethyl chitosan);

(8) Amphoteric polymers of the -D-X-D-X type chosen from:

a) polymers obtained by the action of chloroacetic acid or sodium chloroacetate on compounds comprising at least one unit of formula:

-D-X-D-X-D- (VII)

where D denotes a group

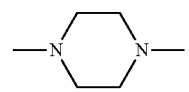

and X denotes the symbol E or E', E or E', which may be identical or different, denote a divalent group that is an alkylene group with a straight or branched chain containing up to 7 carbon atoms in the main chain, which is unsubstituted or substituted with hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X- (VII')

where D denotes a group

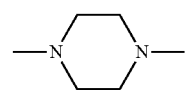

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate;

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers mentioned above that are most particularly preferred according to the invention, mention will be made of those of family (3), such as the copolymers of which the INCI name is Octylacrylamide/acrylates/butylaminoethyl methacrylate copolymer, such as the products sold under the names Amphomer®, Amphomer® LV 71 or Balance® 47 by the company Akzo Nobel and those of family (4), such as the methyl methacrylate/methyl dimethylcarboxymethylammonioethyl methacrylate copolymers sold, for example, under the name Diaformer Z-301N or Z-301W by the company Clariant.

The non-ionic fixing polymers that may be used according to the present invention are chosen, for example, from:
polyalkyloxazolines;
vinyl acetate homopolymers;
vinyl acetate copolymers, for instance copolymers of vinyl acetate and of acrylic ester, copolymers of vinyl acetate and of ethylene, or copolymers of vinyl acetate and of maleic ester, for example of dibutyl maleate;
homopolymers and copolymers of acrylic esters, for instance copolymers of alkyl acrylates and of alkyl methacrylates, such as the products provided by the company Rohm GmbH under the name Eudragit® NE 30 D (INCI name Acrylates copolymer);
copolymers of acrylonitrile and of a non-ionic monomer, chosen, for example, from butadiene and alkyl (meth) acrylates;
styrene homopolymers;
styrene copolymers, for instance copolymers of styrene, of alkyl acrylate and of alkyl methacrylate; copolymers of styrene and of butadiene, or copolymers of styrene, of butadiene and of vinylpyridine;
polyamides;
vinyllactam homopolymers, such as the vinylpyrrolidone homopolymers sold, for example, under the names Luviskol® K30 powder by the company BASF or PVP K3OL or K60 solution or K90 by the company ISP, or such as the polyvinylcaprolactam sold under the name Luviskol® Plus by the company BASF (INCI name PVP);
vinyllactam copolymers, such as a poly(vinylpyrrolidone/vinyllactam) copolymer sold under the trade name Luvitec® VPC 55K65W by the company BASF, poly (vinylpyrrolidone/vinyl acetate) copolymers, such as those sold under the name PVP/VA® S630L, E735, E635 and W735 by the company ISP, Luviskol® VA 73, VA 64 and VA 37 by the company BASF (INCI name VP/VA copolymer); and vinylpyrrolidone/methacrylamide/vinylimidazole terpolymers, for instance the product sold under the name Luviset® Clear by the company BASF (INCI name VP/methacrylamide/vinyl imidazole copolymer).

The alkyl groups of the abovementioned non-ionic polymers preferably contain from 1 to 6 carbon atoms.

According to the invention, it is also possible to use fixing polymers of grafted silicone type comprising a polysiloxane portion and a portion constituted of a non-silicone organic chain, one of the two portions constituting the main chain of the polymer and the other being grafted to said main chain.

These polymers are described, for example, in patent applications EP-A-0 412 704, EP-A-0 412 707, EP-A-0 640 105 and WO 95/00578, EP-A-0 582 152 and WO 93/23009 and patents U.S. Pat. No. 4,693,935, 4,728,571 and U.S. Pat. No. 4,972,037.

These polymers may be amphoteric, anionic or non-ionic, and are preferably anionic or non-ionic.

Such polymers are, for example, copolymers capable of being obtained by radical polymerization starting from the monomer mixture formed:
a) from 50% to 90% by weight of tert-butyl acrylate,
b) from 0% to 40% by weight of acrylic acid,
c) from 5% to 40% by weight of a silicone macromer of formula:

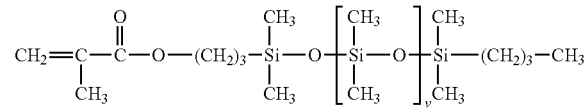

in which v is a number ranging from 5 to 700, the weight percentages being calculated relative to the total weight of the monomers.

Other examples of grafted silicone polymers are in particular polydimethylsiloxanes (PDMSs) to which mixed polymer units of the poly(meth)acrylic acid type and of the poly(alkyl (meth)acrylate) type are grafted via a thiopropylene-type connecting link and polydimethylsiloxanes (PDMSs) to which polymer units of the poly(isobutyl(meth) acrylate) type are grafted via a thiopropylene-type connecting link.

Grafted silicone polymers are, for example, sold under the names Silicone Plus Polymer® VS80 and VA70 by 3M (INCI names Polysilicone-8 and Polysilicone-7 respectively).

Another type of silicone fixing polymer that may be mentioned is the product Luviflex® Silk sold by BASF (INCI name PEG/PPG-25/25 dimethicone/acrylates Copolymer).

Fixing polymers that may also be used are functionalized or non-functionalized, cationic, non-ionic, anionic or amphoteric, silicone or non-silicone polyurethanes, or mixtures thereof.

The polyurethanes particularly targeted by the present invention are those described in patent applications EP 0 751 162, EP 0 637 600, EP 0 648 485 and FR 2 743 297, of which the Applicant is the proprietor, and patent applications EP 0 656 021 and WO 94/03510 from the company BASF and EP 0 619 111 from the company National Starch.

Mention may be made, as polyurethanes particularly suitable in the present invention, of the products sold under the names Luviset PUR® and Luviset® Si PUR by the company BASF (INCI names Polyurethane-1 and Polyurethane-6 respectively).

In one preferred variant, the additional fixing polymer(s) is (are) non-ionic.

Preferably, the additional fixing polymer(s) is (are) water-dispersible or water-soluble.

Even more preferentially, the additional fixing polymer(s) is (are) solubilized in the composition.

For the purpose of the present invention, the term "solubilized polymer" is intended to mean a polymer which, at pH 7 and at 25° C., exhibits a weight solubility in water of greater than or equal to 0.1%, better still greater than or equal to 0.5% and even better still greater than or equal to 1%.

Preferably, the composition according to the invention comprises the additional fixing polymer(s) in an amount ranging from 0.01% to 10% by weight, in particular from 0.01% to 5% by weight and even better still from 0.01% to 1% by weight, relative to the total weight of the composition.

The composition according to the invention preferably comprises an aqueous phase. Preferably, the water content ranges from 10% to 98% by weight, preferably from 20% to 96% by weight, better still from 50% to 96% by weight and even better still from 70% to 96% by weight, relative to the total weight of the composition.

The composition may also comprise one or more organic solvents, such as $C_1$-$C_4$ lower alcohols, such as ethanol, isopropanol, tert-butanol or n-butanol; polyols such as propylene glycol; polyol ethers; $C_5$-$C_{10}$ alkanes, $C_3$-$C_4$ ketones, such as acetone and methyl ethyl ketone; $C_1$-$C_4$ alkyl acetates, such as methyl acetate, ethyl acetate and butyl acetate; dimethoxyethane, diethoxyethane; and mixtures thereof.

The composition of the invention may also comprise at least one customary cosmetic ingredient, in particular chosen from anionic, cationic and non-ionic surfactants, oils; solid fatty substances, and in particular $C_8$-$C_{40}$ esters, $C_8$-$C_{40}$ acids; $C_8$-$C_{40}$ alcohols, sunscreens; moisturizing agents; antidandruff agents; antioxidants; chelating agents; pearlescent agents and opacifiers; plasticizers or coalescence agents; fillers, in particular inorganic fillers; glitter flakes; silicones, in particular silicone gums, alkoxylated or non-alkoxylated silicones; polymeric or non-polymeric thickeners or gelling agents, other than the cellulose-based thickening polymers; emulsifiers; polymers, other than those previously mentioned, in particular conditioning polymers; fragrances; preservatives; basifying agents, such as sodium hydroxide, or acidifying agents; silanes; crosslinking agents; or dyes. The composition can, of course, comprise several cosmetic ingredients appearing in the above list.

Depending on their nature and the purpose of the composition, the normal cosmetic ingredients can be present in normal amounts which can be easily determined by those skilled in the art and which can be, for each ingredient, between 0.01% and 80% by weight. Those skilled in the art will take care to choose the ingredients included in the composition and the amounts thereof so that they do not harm the properties of the compositions of the present invention.

The compositions in accordance with the invention can be packaged for example in a jar, in a tube, in a pump-dispenser bottle, in a foamer or in an aerosol device that is customary in the cosmetics industry.

The compositions according to the invention can, when they are intended to be packaged in an aerosol device, contain one or more propellant gases.

The propellant gas can then be chosen, for example, from volatile hydrocarbons, such as, in particular, $C_1$ to $C_4$ alkanes and preferably n-butane, propane, isobutane and mixtures thereof, chlorinated and/or fluorinated hydrocarbons, dimethyl ether and mixtures of these gases.

When it contains same, the composition comprises a propellant gas in a content ranging from 1% to 50% by weight and more preferentially from 1% to 10% by weight, relative to the total weight of said composition.

The compositions according to the invention can be, inter alia, in the form of liquids which are thickened to a lesser or greater extent, of gels, of creams, of pastes or of foams.

They are preferably in the form of foams generated by an aerosol or a foamer.

The composition according to the invention may be advantageously used for cosmetic hair treatment. In particular, it may be used for hairstyling, for example for shaping and/or fixing the hairstyle.

According to one particularly preferred embodiment, it is used for simultaneously styling and conditioning the hair.

The present invention also relates to a cosmetic treatment process for the hair, for example a hair care process, or a process for shaping and/or retaining the shape of the hairstyle, which consists in applying, to the hair, an effective amount of a composition as described above and then optionally carrying out rinsing after an optional leave-on time.

Preferably, the composition according to the invention is not rinsed off.

The invention also relates to a cosmetic set for shaping keratin fibres, capable of forming a volume-expanded composition, comprising:
a composition such as that which has just been described; and
a volume-expanded composition dispenser, for delivering said composition in the form of a volume-expanded composition.

The dispenser may be a bottle of foamer type or else an aerosol device, the composition then comprising, in the latter case, at least one propellant gas.

The dispensers of foamer type comprise a container for containing the composition and a dispensing head for delivering the composition. The foam is formed by forcing the composition to pass through a material comprising a porous substance such as a sintered material, a filtering grid made of plastic or of metal, or similar structures. The container comprises either a squeezable wall or a pump and a dip tube for transferring the composition from the container into the head in order to deliver the product.

The examples that follow are given as illustrations of the present invention. In these examples, all the amounts are indicated as weight percentages of active material (AM) relative to the total weight of the composition.

Foams in a Foamer

| INCI Name | Trade Names | Composition 1 | Composition 2 |
|---|---|---|---|
| VINYLAMINE/VINYLFORMAMIDE COPOLYMER | LUVIQUAT 9030 (BASF) (13% AM) | 0.19 | 0.26 |
| POLYQUATERNIUM-4 | CELQUAT LOR (AKZO NOBEL) | 0.5 | — |

-continued

| INCI Name | Trade Names | Composition 1 | Composition 2 |
|---|---|---|---|
| POLYQUATERNIUM-68 | LUVIQUAT SUPREME (BASF) (20% AM) | — | 0.2 |
| VP/DIMETHYLAMINOETHYL-METHACRYLATE COPOLYMER | COPOLYMER 845-O (ISP) (19.85% AM) | — | 0.5 |
| HYDROXYETHYLCELLULOSE | NATROSOL 250 HHR PC (ASHLAND) | 0.05 | 0.1 |
| SODIUM COCOAMPHOACETATE | MIRANOL ULTRA C 32 (RHODIA) (32% AM) | 0.09 | — |
| COCAMIDOPROPYL BETAINE | TEGO BETAIN F 50 (EVONIK GOLDSCHMIDT) (38% AM) | — | 0.26 |
| PEG-40 HYDROGENATED CASTOR OIL | EUMULGIN HRE 40 (BASF) | 0.8 | 1 |
| PROPYLENE GLYCOL | PROPYLENE GLYCOL USP/EP (DOW CHEMICAL) | 3 | — |
| FRAGRANCE | | 0.2 | 0.3 |
| PRESERVATIVES | | 0.7 | 0.9 |
| LACTIC ACID | PURAC HS88 (PURAC) | 0.01 | — |
| WATER | | qs 100 g | qs 100 g |

Pressurized Foams

| INCI Name | Trade Names (supplier) | Composition 3 | Composition 4 |
|---|---|---|---|
| VINYLAMINE/VINYLFORMAMIDE COPOLYMER | LUVIQUAT 9030 (BASF) (13% AM) | 0.06 | 0.13 |
| POLYQUATERNIUM-46 | LUVIQUAT HOLD AT 2 (BASF) (20% AM) | 0.06 | — |
| POLYQUATERNIUM-68 | LUVIQUAT SUPREME (BASF) (20% AM) | — | 0.4 |
| VINYL CAPROLACTAM/VP/DIMETHYLAMINOETHYL METHACRYLATE COPOLYMER | ADVANTAGE HC 37 (ISP) (37% AM) | — | 0.37 |
| VP/VA COPOLYMER | LUVISKOL VA 64 W (BASF) (50% AM) | 0.5 | |
| HYDROXYETHYLCELLULOSE | NATROSOL 250 HHR PC (ASHLAND) | 0.2 | 0.1 |
| DISODIUM COCOAMPHODIACETATE | MIRANOL C2M CONC NP (RHODIA) (31.5%) | 0.22 | |
| HYDROXYETHYL CARBOXYMETHYL COCAMIDOPROPYLAMINE | CHIMEXANE HA (CHIMEX) (36.5% AM) | | 0.22 |
| PEG-40 HYDROGENATED CASTOR OIL | EUMULGIN HRE 40 (BASF) | 1.5 | — |
| PROPYLENE GLYCOL | PROPYLENE GLYCOL USP/EP (DOW CHEMICAL) | 2 | — |
| FRAGRANCE | | 0.3 | — |
| PRESERVATIVES | | 0.8 | |
| ALCOHOL | ETHYL ALCOHOL SURFIN 99.9 DENATURED (FRANCE ALCOOLS) | — | 10 |
| HYDROCHLORIC ACID | SQ HYDROCHLORIC ACID (QUALIGENS FINE CHEMICALS) | 0.001 | — |
| HYDROCARBONS | PROPEL 45 (REPSOL) | 5 | 4.5 |
| HYDROFLUOROCARBON 152A | DYMEL 152 A (DUPONT) | — | 1.5 |
| WATER | | qs 100 g | qs 100 g |

Compositions 1 to 4 are prepared. On application to the hair, expanded foams are obtained which make it possible to obtain good styling and cosmetic properties with, in particular, long-lasting fixing over time and a pleasant feel.

The invention claimed is:

1. A foaming cosmetic composition comprising:
at least one vinylformamide/vinylformamine copolymer comprising:
from 10 to 95 mol % of units of the following formula A1:

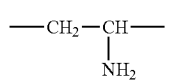

(A1)

and
from 90 to 5 mol % of units of the following formula A2:

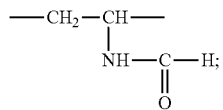

(A2)

at least one cellulose-based thickening polymer chosen from hydroxyethylcelluloses, wherein the total amount of cellulose-based thickening polymer ranges from about 0.04% to about 1% by weight, relative to the total weight of the composition;
at least one amphoteric or zwitterionic surfactant; and
at least one additional fixing polymer chosen from anionic, cationic, amphoteric, or non-ionic polymers.

2. The composition according to claim 1, wherein the at least one vinylformamide/vinylformamine copolymer comprises from about 10 to about 60 mol % of units of formula A1.

3. The composition according to claim 1, wherein the at least one vinylformamide/vinylformamine copolymer comprises from about 20 to about 40 mol % of units of formula A1.

4. The composition according to claim 1, wherein the at least one vinylformamide/vinylformamine copolymer comprises at least one additional monomer unit representing less than about 20 mol % of the at least one vinylformamide/vinylformamine copolymer.

5. The composition according to claim 1, wherein the at least one vinylformamide/vinylformamine copolymer consists essentially of units of formula A1 and of units of formula A2.

6. The composition according to claim 1, wherein the total amount of vinylformamide/vinylformamine copolymer ranges from about 0.01% to about 20% by weight, relative to the total weight of the composition.

7. The composition according to claim 1, wherein the amphoteric or zwitterionic surfactant is chosen from betaines, cocoamidopropyl betaine, or products having the following respective structures (IA), (IB), or (IC):

$$R_a\text{—CON(Z)CH}_2\text{—(CH}_2)_m\text{—N}^{+(R_b)}(R_c)(CH_2COO^-) \quad (IA)$$

wherein:
$R_a$ is chosen from a $C_{10}$-$C_{30}$ alkyl or alkenyl group derived from an acid $R_a$—COON optionally present in hydrolysed coconut oil, or a heptyl, nonyl, or undecyl group, $R_b$ represents a β-hydroxyethyl group,
$R_c$ represents a carboxymethyl group,
m is equal to 0, 1 or 2, and
Z is chosen from a hydrogen atom or a hydroxyethyl or carboxymethyl group;

$$R_{a'}\text{—CON(Z)CH}_2\text{—(CH}_2)_{m'}\text{—N(B)(B')} \quad (IB)$$

wherein:
B represents —CH$_2$CH$_2$OX',
X' is chosen from —CH$_2$—COOH, CH$_2$—COOZ', —CH$_2$CH$_2$—COOH, —CH$_2$CH$_2$—COOZ', or a hydrogen atom,
B' is chosen from —(CH$_2$)$_z$—Y', with z=1 or 2,
Y' is chosen from —COON, —COOZ', —CH$_2$—CHOH—SO$_3$H, or —CH$_2$—CHOH—SO$_3$Z',
Z' is chosen from an ion resulting from an alkali metal or alkaline-earth metal, sodium, potassium, or magnesium; an ammonium ion; or an ion resulting from an organic amine, an amino alcohol, monoethanolamine, diethanolamine, triethanolamine, monoisopropanolamine, diisopropanolamine, triisopropanolamine, 2-amino-2-methyl-1-propanol, 2-amino-2-methyl-1,3-propanediol, or tris(hydroxymethyl)aminomethane,
$R_{a'}$ represents a $C_{10}$-$C_{30}$ alkyl or alkenyl group of an acid $R_a$COOH optionally present in hydrolysed linseed oil or coconut oil, an alkyl group, a $C_{17}$ alkyl group, an iso $C_{17}$ alkyl group, or an unsaturated $C_{17}$ group,
m' is equal to 0, 1 or 2, and
Z is chosen from a hydrogen atom or a hydroxyethyl or carboxymethyl group;

$$R_{a''}\text{—NH—CH(Y'')—(CH}_2)_n\text{-C(O)—NH—(CH}_2)_{n'}\text{—N(R}_d)(R_e) \quad (IC)$$

wherein:
$R_{a''}$ is chosen from a $C_{10}$-$C_{30}$ alkyl or alkenyl group of an acid
$R_a$—C(O)OH, which is optionally present in hydrolysed linseed oil or coconut oil;
Y" is chosen from —C(O)OH, —C(O)OZ", —CH$_2$—CH(OH)—SO$_3$H, or —CH$_2$—CH(OH)—SO$_3$—Z", with Z" chosen from a cationic counterion resulting from an alkali metal or alkaline-earth metal, sodium, an ammonium ion, or an ion resulting from an organic amine;
$R_d$ and $R_e$ represent, independently of each other, a $C_1$-$C_4$ alkyl or hydroxyalkyl radical; and
n and n' denote, independently of each other, an integer ranging from 1 to 3.

8. The composition according to claim 1, wherein the total amount of amphoteric and zwitterionic surfactant ranges from about 0.01% to about 20% by weight, relative to the total weight of the composition.

9. The composition according to claim 1, wherein the weight ratio of the total amount of amphoteric and zwitterionic surfactant to the total amount of cellulose-based thickening polymer ranges from about 0.01 to about 10.

10. The composition according to claim 1, wherein the at least one additional fixing polymer is chosen from cationic or non-ionic polymers.

11. The composition according to claim 1, further comprising water in an amount ranging from about 10% to about 98% by weight, relative to the total weight of the composition.

12. The composition according to claim 1, wherein the composition is a non-washing composition comprising less than about 5% by weight of surfactant chosen from anionic surfactants and non-ionic surfactants.

13. The composition according to claim 1, further comprising a propellant gas chosen from volatile hydrocarbons, C₁ to C₄ alkanes, n-butane, propane, isobutane, or mixtures thereof; or chlorinated and/or fluorinated hydrocarbons, dimethyl ether, or mixtures of these gases;
    wherein the total amount of propellant gas ranges from about 1% to about 50% by weight, relative to the total weight of the composition.

14. A cosmetic treatment process for the hair, comprising:
applying to the hair, an effective amount of a foaming composition comprising:
    at least one vinylformamide/vinylformamine copolymer comprising:
        from 10 to 95 mol % of units of the following formula A1:

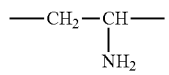
(A1)

and
        from 90 to 5 mol % of units of the following formula A2:

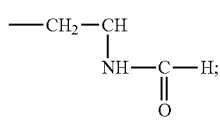
(A2)

at least one cellulose-based thickening polymer chosen from hydroxyethylcelluloses, wherein the total amount of cellulose-based thickening polymer ranges from about 0.04% to about 1% by weight, relative to the total weight of the composition;
    at least one amphoteric or zwitterionic surfactant; and
    at least one additional fixing polymer chosen from anionic, cationic, amphoteric, or non-ionic polymers; and
optionally rinsing after an optional leave-on time.

15. The cosmetic treatment process for the hair according to claim 14, wherein the composition is in the form of a foam.

16. A cosmetic set for shaping keratin fibers, capable of forming a volume-expanded composition, the set comprising:
a composition comprising:
    at least one vinylformamide/vinylformamine copolymer comprising:
        from 10 to 95 mol % of units of the following formula A1:

and
    from 90 to 5 mol % of units of the following formula A2:

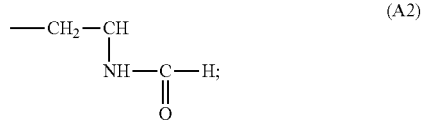

at least one cellulose-based thickening polymer chosen from hydroxyethylcelluloses, wherein the total amount of cellulose-based thickening polymer ranges from about 0.04% to about 1% by weight, relative to the total weight of the composition;
    at least one amphoteric or zwitterionic surfactant; and
    at least one additional fixing polymer chosen from anionic, cationic, amphoteric, or non-ionic polymers; and
a volume-expanded composition dispenser configured to deliver the composition in the form of a volume-expanded composition.

17. The cosmetic set according to claim 16, wherein the dispenser is an aerosol dispenser, and the composition further comprises at least one propellant gas.

18. The cosmetic set according to claim 16, wherein the dispenser is a foamer.

\* \* \* \* \*